US008498884B2

(12) United States Patent
Maitland et al.

(10) Patent No.: US 8,498,884 B2
(45) Date of Patent: Jul. 30, 2013

(54) ENCRYPTED PORTABLE ELECTRONIC MEDICAL RECORD SYSTEM

(75) Inventors: Vic Maitland, Fort Lauderdale, FL (US); Michael Angelillo, Fort Lauderdale, FL (US); Ed Cramer, Fort Lauderdale, FL (US); Kurt Miller, Fort Lauderdale, FL (US)

(73) Assignee: Universal Healthcare Network, LLC, FL (US)

( * ) Notice: Subject to any disclaimer, the term of this patent is extended or adjusted under 35 U.S.C. 154(b) by 0 days.

(21) Appl. No.: 13/052,682

(22) Filed: Mar. 21, 2011

(65) Prior Publication Data

US 2012/0209624 A1    Aug. 16, 2012

Related U.S. Application Data

(60) Provisional application No. 61/315,527, filed on Mar. 19, 2010.

(51) Int. Cl.
*A61B 5/00* (2006.01)
(52) U.S. Cl.
USPC .................................. 705/3; 705/2; 713/193
(58) Field of Classification Search
USPC ............................. 705/3; 713/193
See application file for complete search history.

(56) References Cited

U.S. PATENT DOCUMENTS

| | | | |
|---|---|---|---|
| 3,970,996 A | 7/1976 | Yasaka et al. | |
| 5,724,379 A | 3/1998 | Perkins et al. | |
| 5,822,544 A | 10/1998 | Chaco et al. | |
| 5,899,998 A | 5/1999 | McGauley et al. | |
| 6,021,393 A | 2/2000 | Honda et al. | |
| 6,488,205 B1 | 12/2002 | Jacobson | |
| 6,662,999 B1 | 12/2003 | Vancour et al. | |
| 7,395,215 B2 | 7/2008 | Grushka | |
| 7,770,026 B2 * | 8/2010 | Ebitani et al. ................ | 713/193 |
| 2002/0077861 A1 * | 6/2002 | Hogan .............................. | 705/3 |
| 2003/0040940 A1 * | 2/2003 | Nehammer ....................... | 705/3 |
| 2003/0204417 A1 | 10/2003 | Mize | |
| 2003/0220822 A1 | 11/2003 | Fiala et al. | |
| 2004/0199408 A1 | 10/2004 | Johnson | |
| 2005/0197859 A1 | 9/2005 | Wilson et al. | |
| 2005/0216313 A1 * | 9/2005 | Claud et al. ....................... | 705/3 |
| 2006/0074713 A1 | 4/2006 | Conry et al. | |
| 2006/0111940 A1 | 5/2006 | Johnson et al. | |
| 2007/0088564 A1 | 4/2007 | March, Jr. et al. | |
| 2007/0100664 A1 | 5/2007 | Seib et al. | |
| 2007/0129969 A1 | 6/2007 | Burdick et al. | |
| 2007/0158411 A1 | 7/2007 | Krieg, Jr. | |
| 2008/0109261 A1 | 5/2008 | Kobayashi et al. | |

(Continued)

OTHER PUBLICATIONS

Google patents search, Mar. 1, 2013.*

*Primary Examiner* — Dilek B Cobanoglu
(74) *Attorney, Agent, or Firm* — David P. Lhota, Esq.; Lhota & Associates, P.A.

(57) ABSTRACT

A portable, electronic and encrypted medical record device and management system that receives and stores a registrant's or patient's medical history in a secured database, records the medical history on a portable computer readable medical storage device, includes a multi-level encrypted security system to control access to the medical information on the storage device or in the system for authorizing modification or access to the medical information, allows authorized medical personnel to update recently acquired medical data, dictates the data that authorized medical entities or personnel have access to and includes a recognizable logo to alert medical personnel of the medical storage device.

15 Claims, 18 Drawing Sheets

U.S. PATENT DOCUMENTS

2008/0183504 A1 7/2008 Highley
2008/0306774 A1 12/2008 George et al.
2008/0319798 A1 12/2008 Kelley
2009/0019552 A1 1/2009 McLaughlin et al.
2009/0144200 A1 6/2009 Yoshioka
2009/0164243 A1 6/2009 Zubak et al.

* cited by examiner

EHR System Overview Figure 1
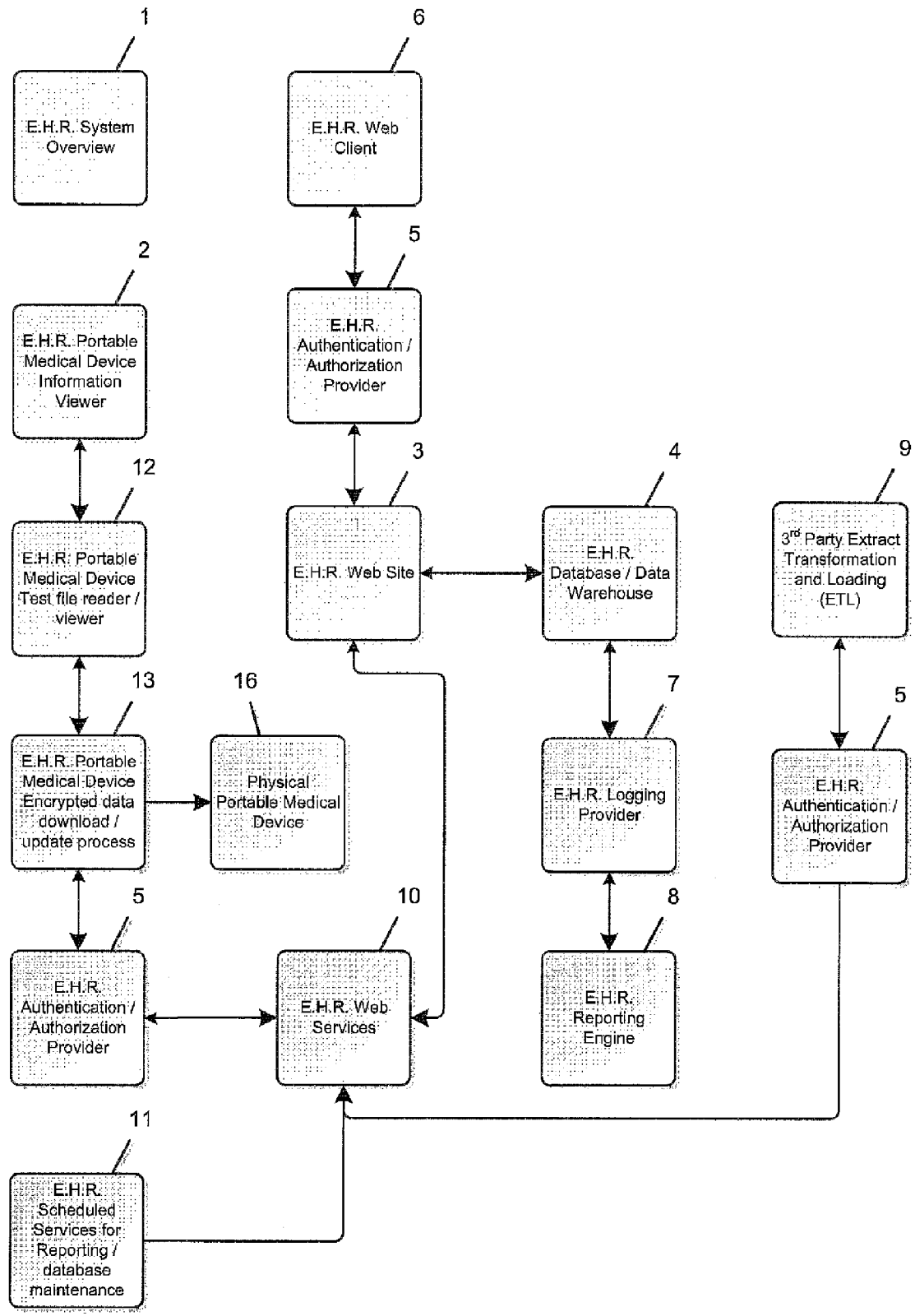

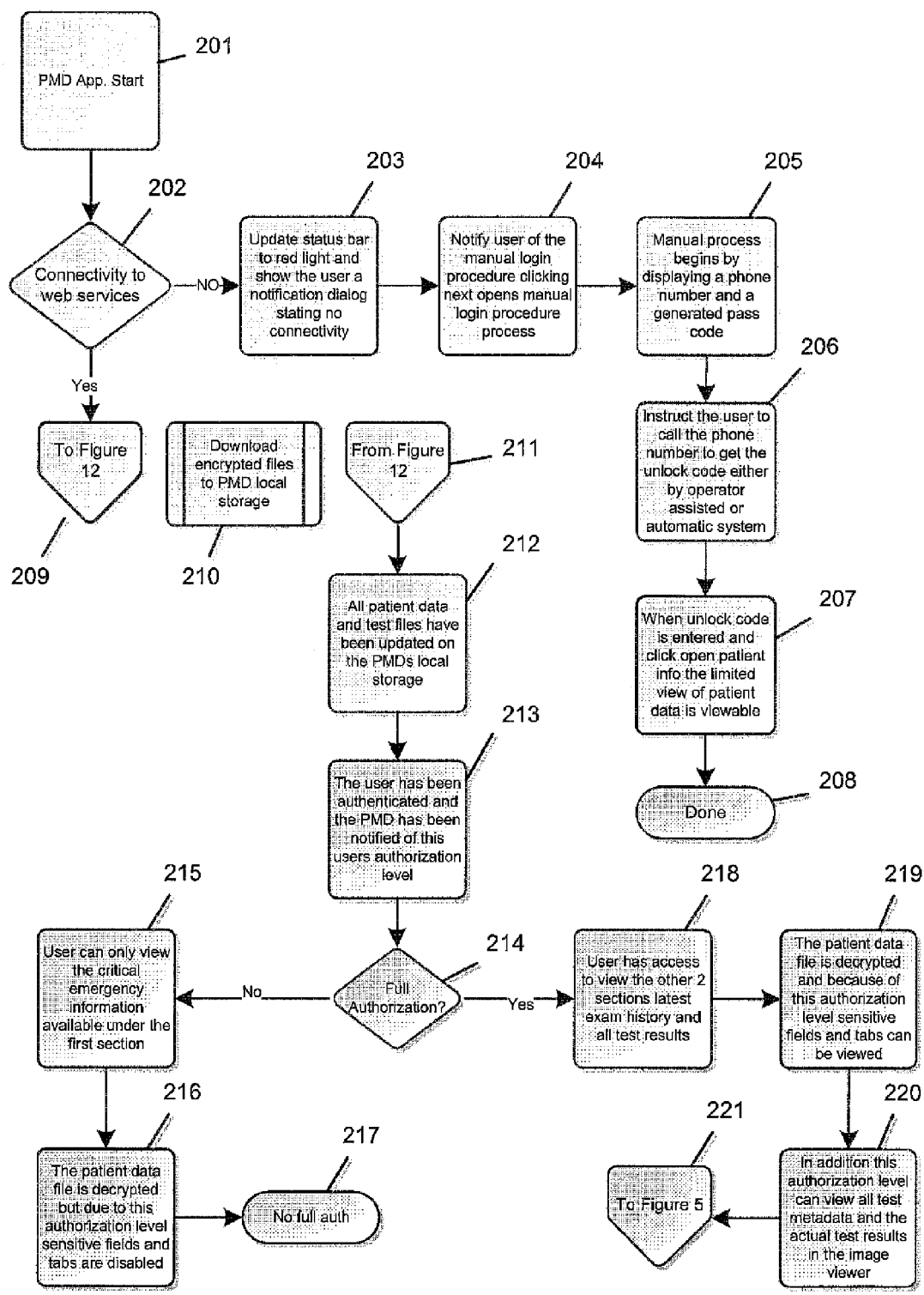
EHR System Portable Medical Device (PMD) Application Data Viewer Figure 2

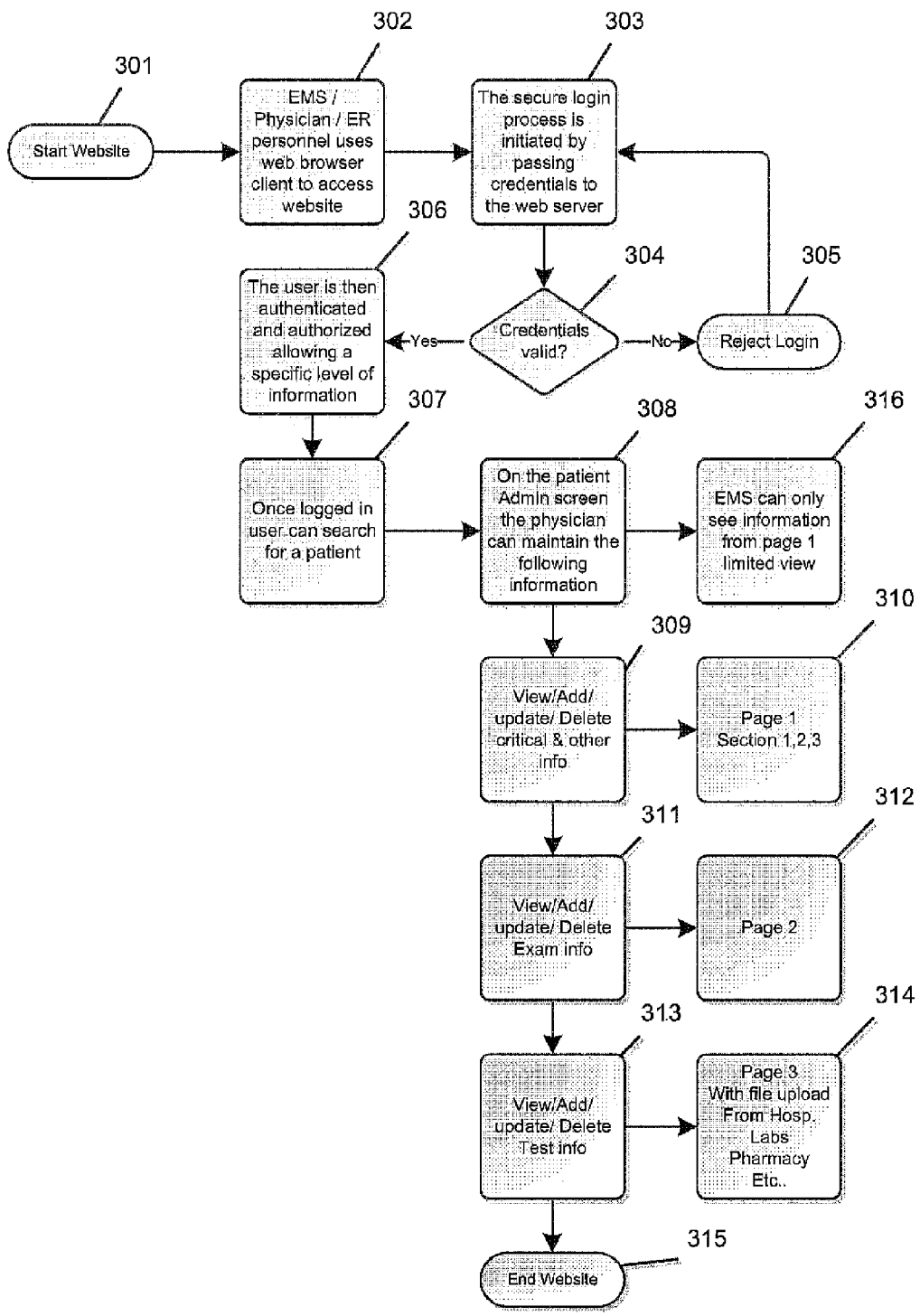
EHR System SSL Secure Website Figure 3

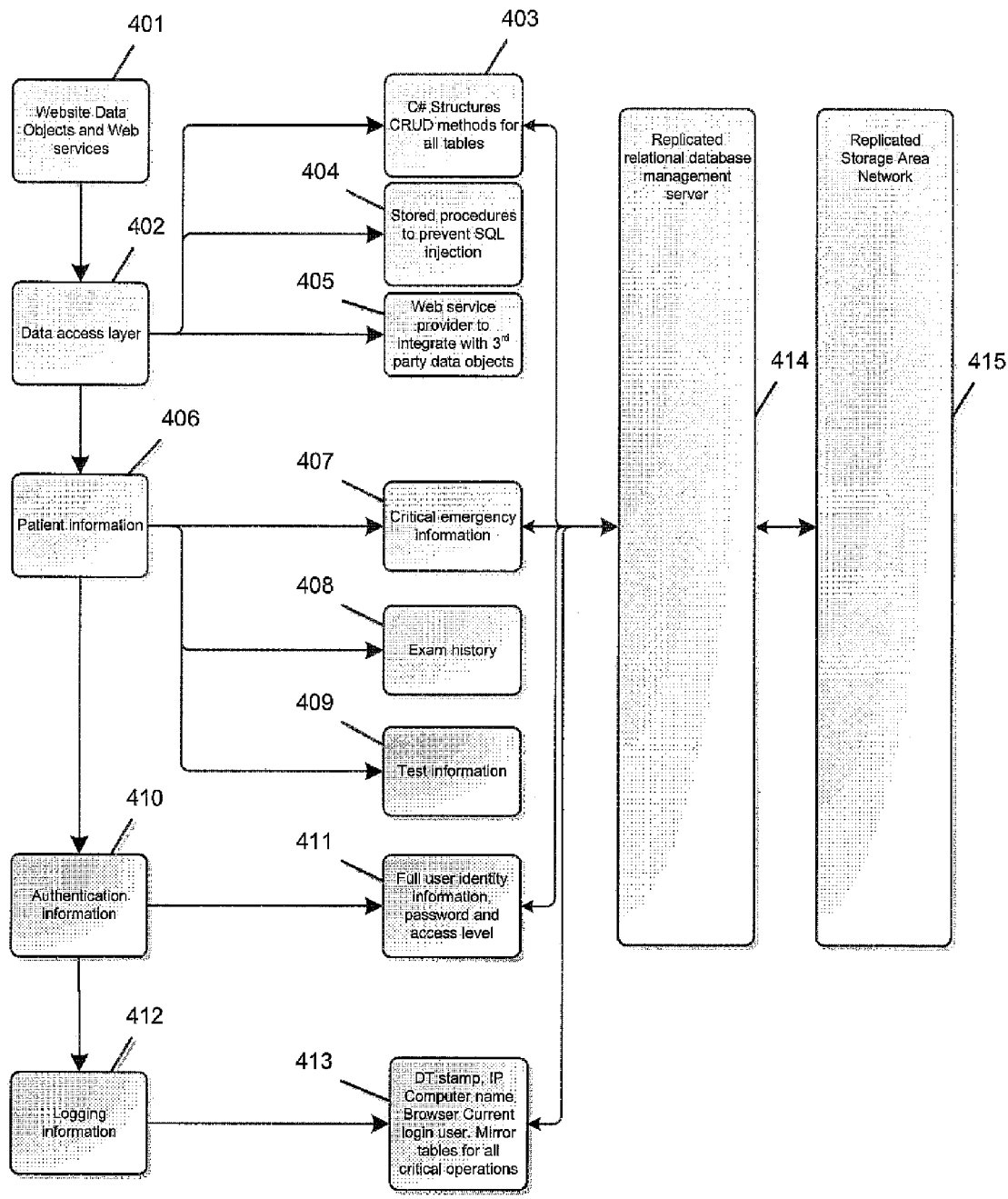
EHR System Database / Data Warehouse Figure 4

EHR System Authentication and Authorization Provider  Figure 5
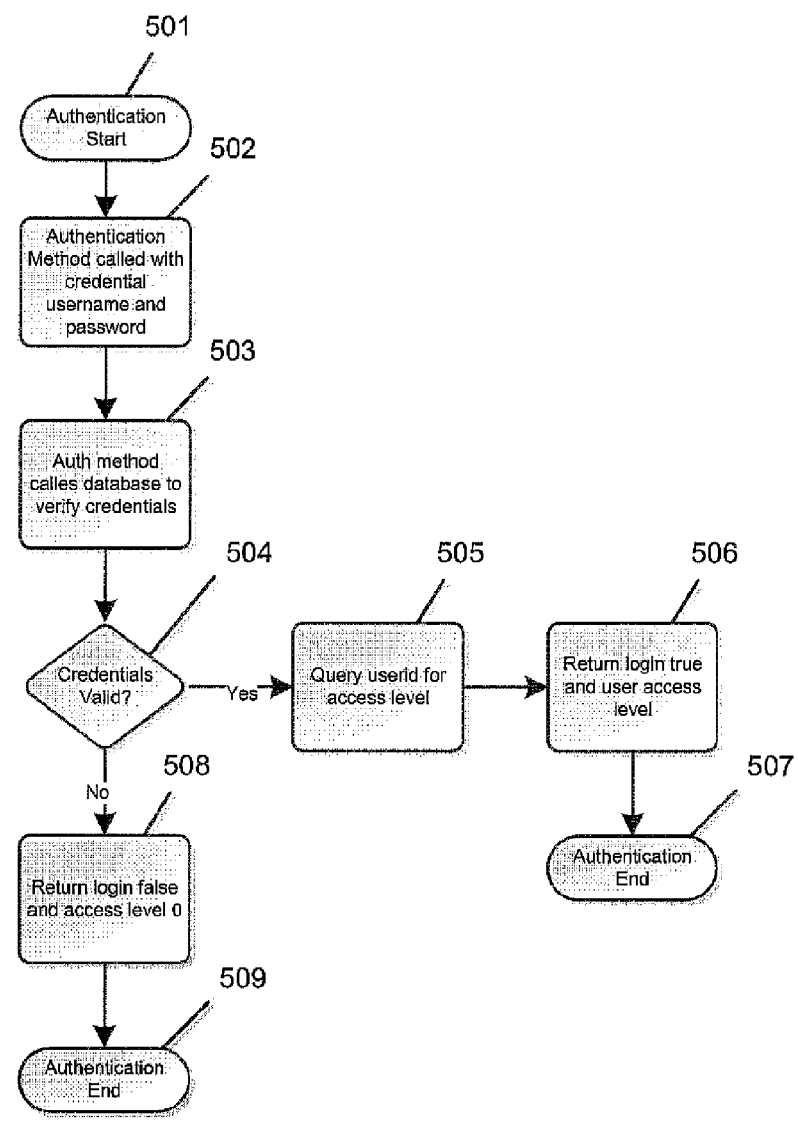

EHR System Web Client Figure 6
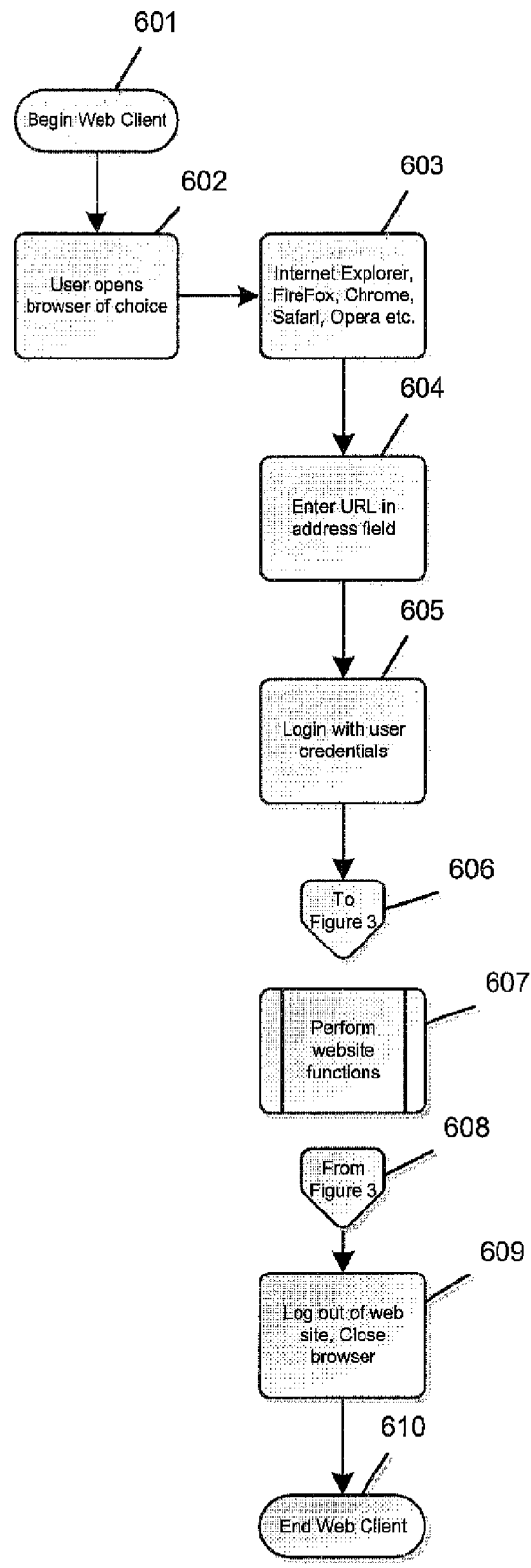

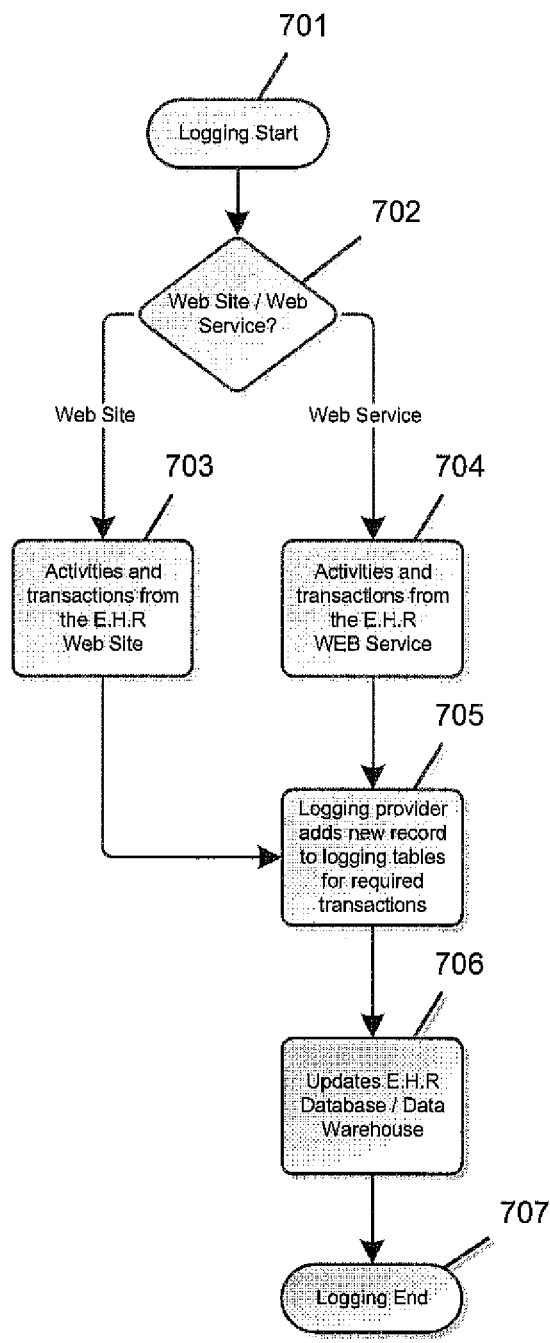
EHR System Logging Provider Figure 7

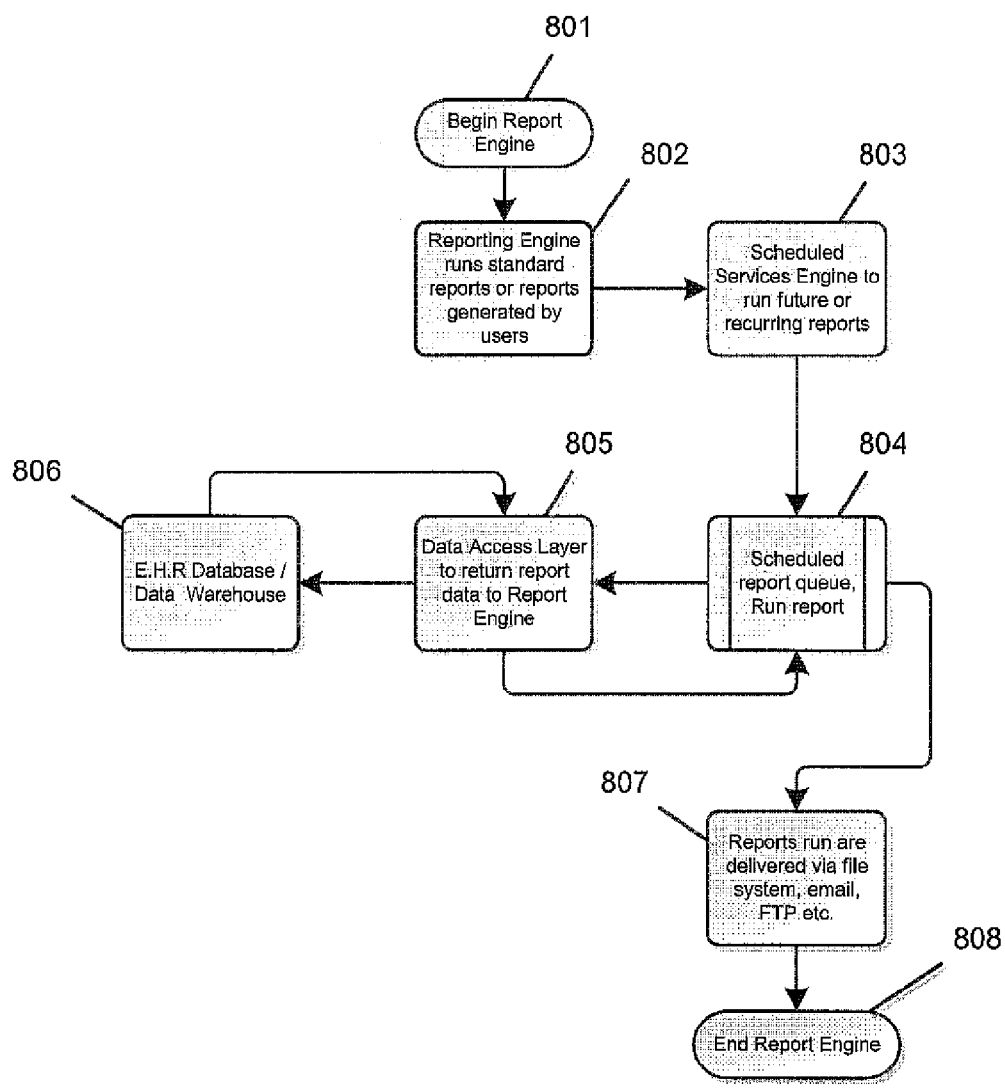
EHR System Reporting Engine  Figure 8

EHR System Extraction Transformation and Loading  Figure 9
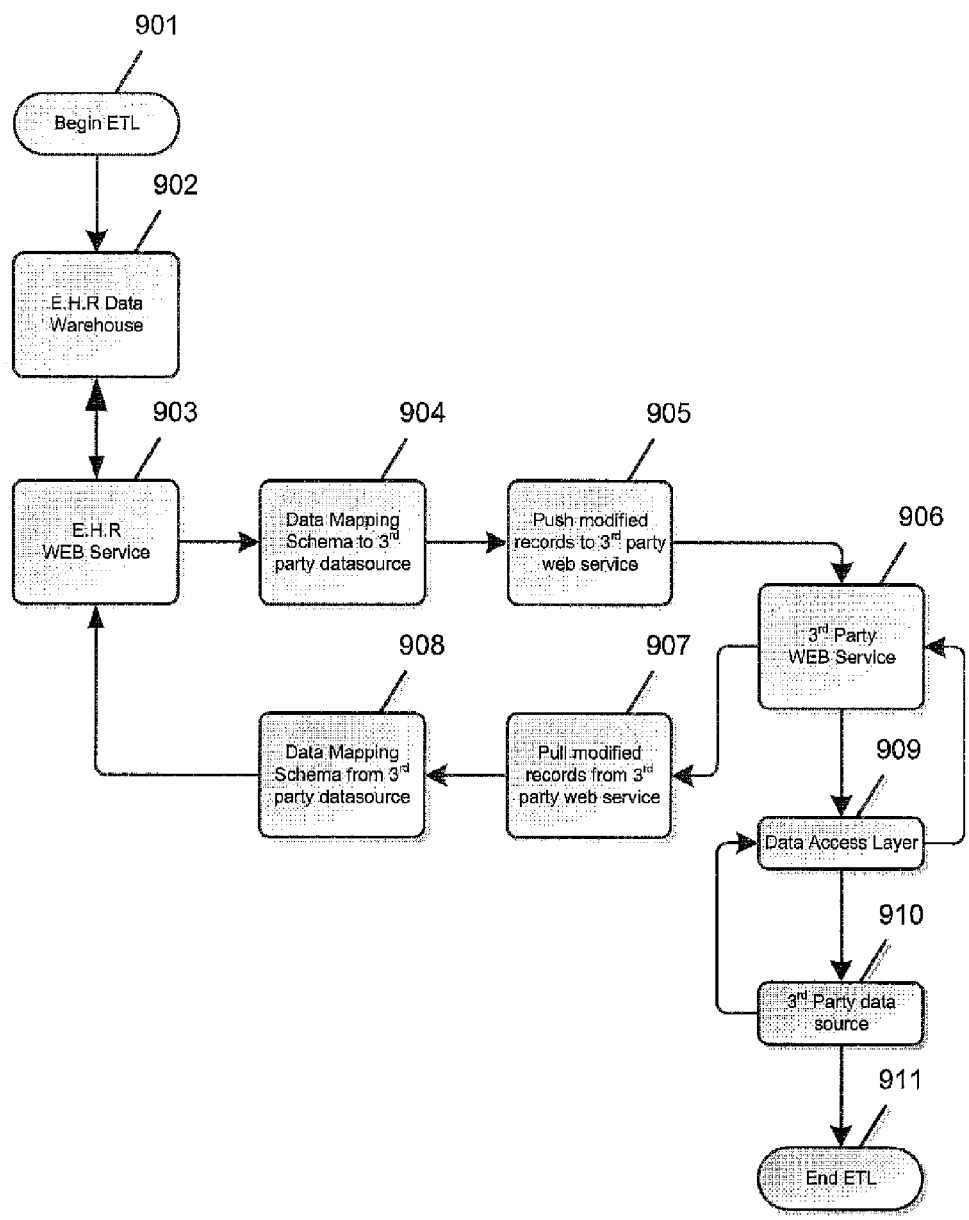

EHR System Web Services  Figure 10
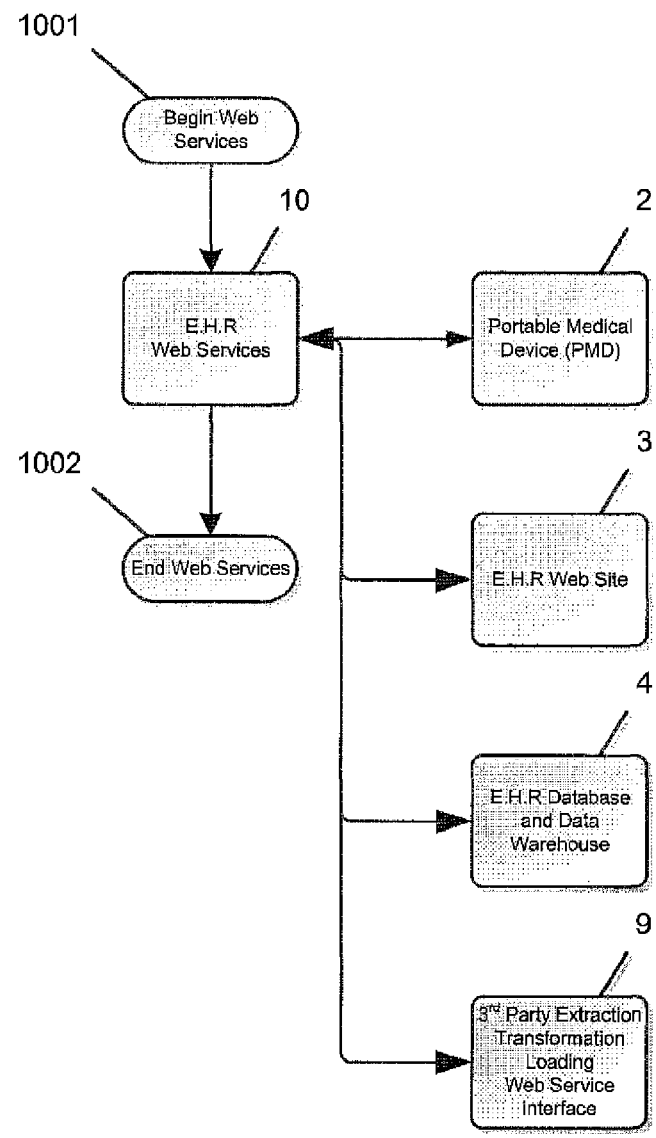

EHR System Scheduled Services Figure 11
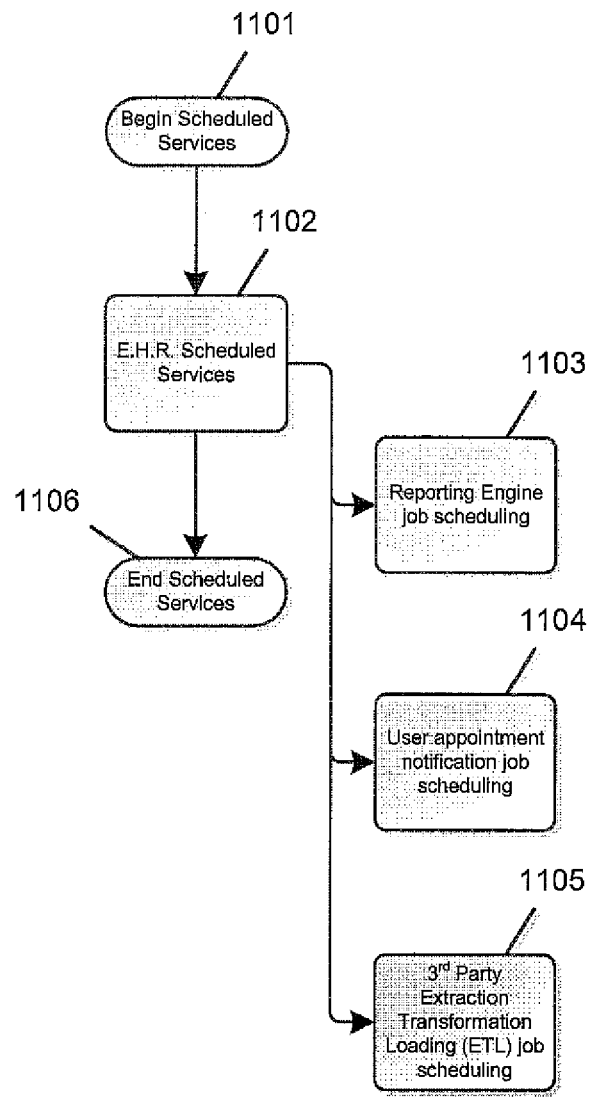

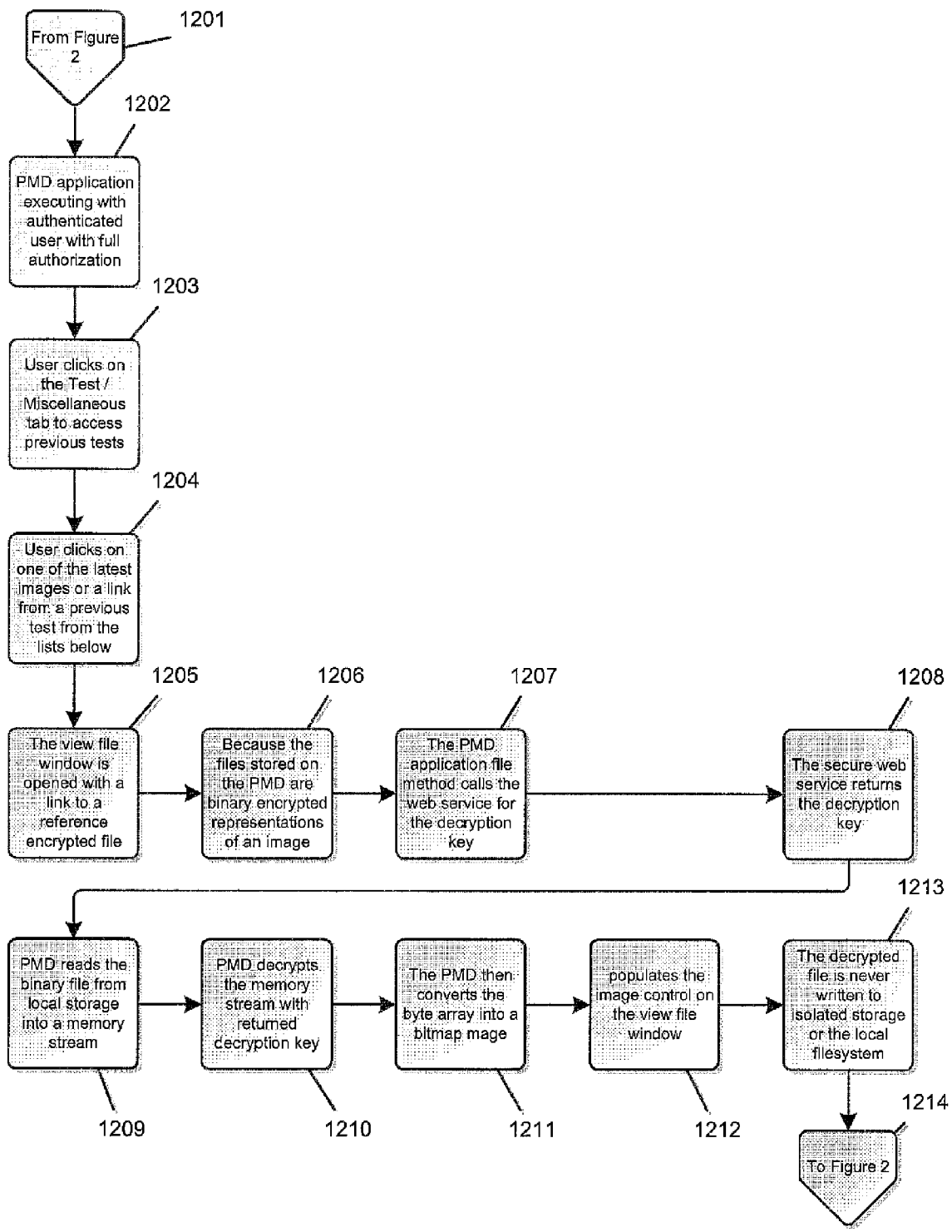
EHR System Portable Medical Device Test file read Figure 12

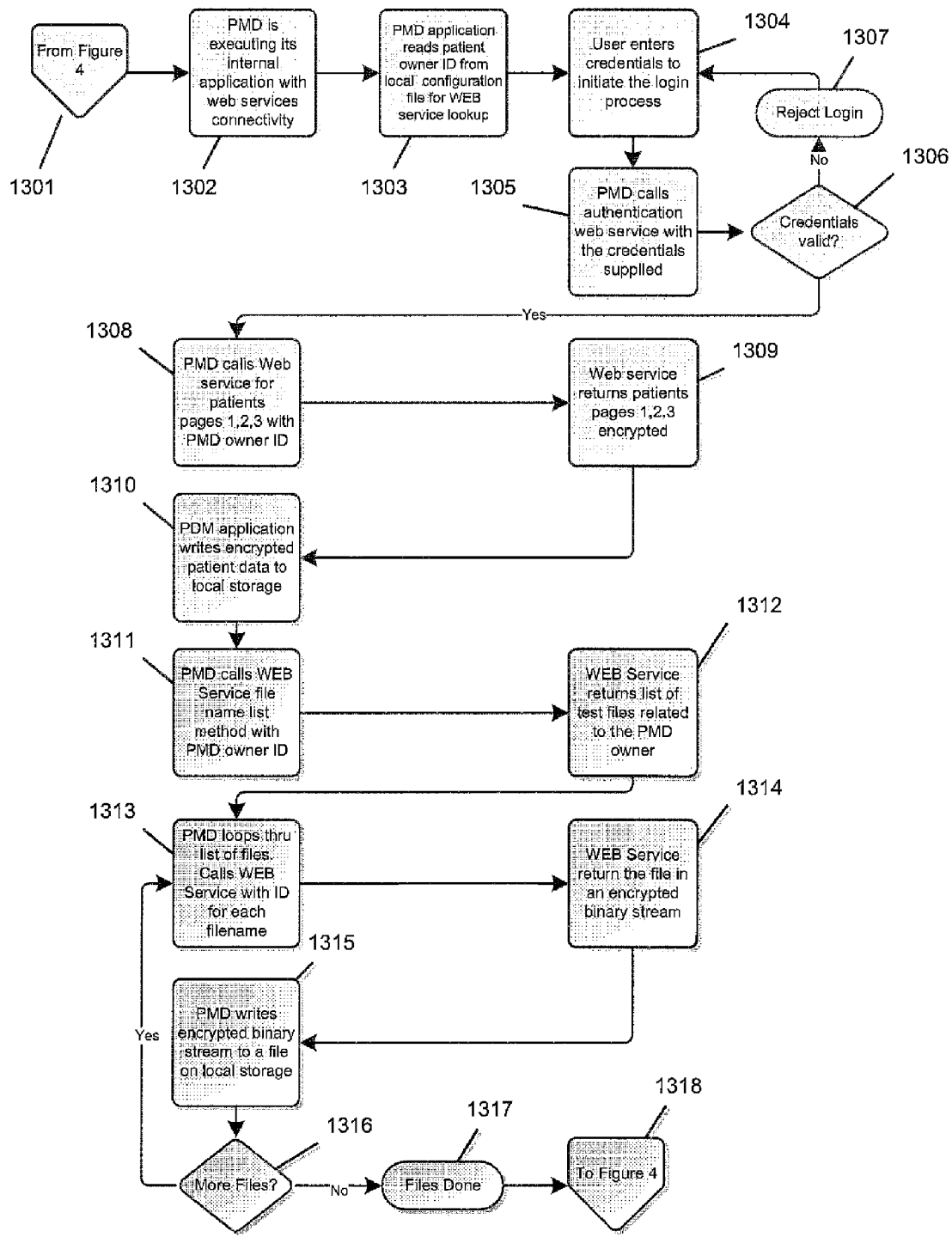
EHR System Web Service API Encrypted Data Download to PMD  Figure 13

EHR System Form Page 1 Figure 14a

Emergency Health Record ™

[Print Form]

The Patient's Name Stated Has Given Full Authorization To Use The Information Provided to Facilitate Medical Care First Name [ ]   Initial [ ]   Last Name [ ]

Patient's DOB [ ]   Driver's License # [ ]   SSN# [ ]   Gender [ ]
Language Spoken [ ]   Religion [ ]   Weight (in LBS) [ ]   Height (ft./In.) [ ]

Emergency Contact Name [ ]   Physician Name [ ]
Emergency Contact Phone # [ ]   Physician Phone # [ ]
   Hospital Affiliation [ ]
Medical Power of Attorney Name [ ]   Insurance Name [ ]
Medical Power of Attorney Phone # [ ]   Insurance Number [ ]
Name of Executor of Living Will [ ]   Executor of Living Will Phone # [ ]

Critical Emergency Information ™

DNR STATUS............................................................................. [ ]

| | No | Yes | | |
|---|---|---|---|---|
| AIDS Status | ☐ | ☐ | Blood Type | [ ] |
| Are You Taking Blood Thinners? | ☐ | ☐ | 1401 | |
| Dialysis Patient | ☐ | ☒ | Patient's Photo | |
| Stroke Patient | ☐ | ☐ | | |
| Epileptic Patient | ☐ | ☐ | | |
| Diabetic Patient | ☐ | ☐ | | |
| Heart Patient | ☐ | ☐ | | |
| Asthma Patient | ☐ | ☐ | | |
| Can You Have A MRI | ☐ | ☐ | | |
| Organ Donor | ☐ | ☐ | | |
| False Teeth / Dentures | ☐ | ☐ | If Yes What? | [ ] |
| Eye Glasses / Contacts | ☐ | ☐ | If Yes What? | [ ] |
| Pacemaker Present | ☐ | ☐ | Type | [ ] |
| Defibrillator Present | ☐ | ☐ | Type | [ ] |
| Organ Recipient | ☐ | ☐ | If Yes What? | [ ] |
| Contagious Dx | ☐ | ☐ | If Yes What? | [ ] |
| Drug Allergies | ☐ | ☐ | If Yes What? | [ ] |
| Food Allergies | ☐ | ☐ | If Yes What? | [ ] |

Current Medications / Dosage: [ ]

© 2009 Emergency Health Record, LLC
All Rights Reserved   Patent Pending

EHR System Form Page 2 Figure 14b

Latest Updated History and Physical Exam

| Patient's Name | |
| Present Illness | |
| Past Medical History | |
| Immunizations | |
| Allergies | |
| Past Surgical History | |
| Social History | |
| Family Medical History | |
| Review of Systems | |

1402

Vital Signs: BP: [ ] Pulse: [ ] Temp: [ ]

| Skin: | |
| Heent: | |
| Breast: | |
| Respiratory: | |
| Heart: | |
| Gastrointestinal: | |
| Genitalia: | |
| Rectal Exam: | |
| Musculoskeletal: | |
| Vascular: | |
| Neurological: | |
| Mental Status: | |
| Impression / Plan: | |

Signature: _____ Date: _____

© 2009 Emergency Health Record, LLC
All Rights Reserved. Patent Pending

EHR System Form Page 3 Figure 14c
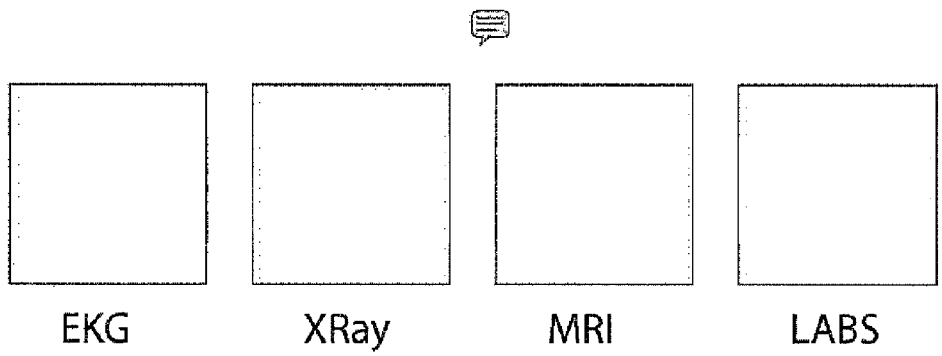
1403

EHR System PMD Application Screen Shots Figure 15a

EHR System PMD Application Screen Shots cont. Figure 15b
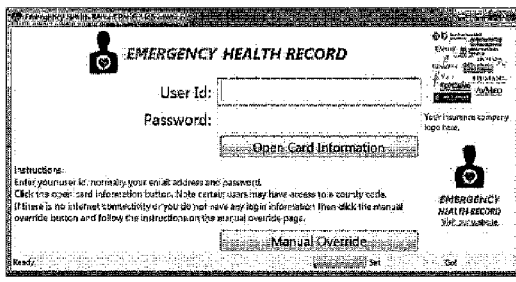
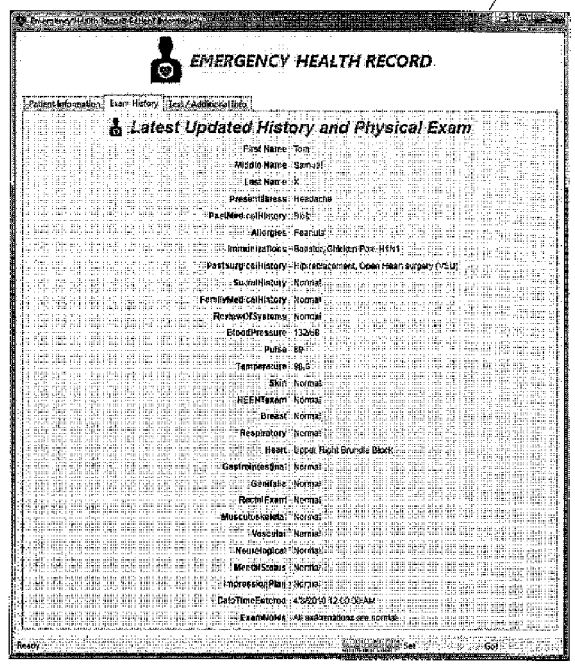
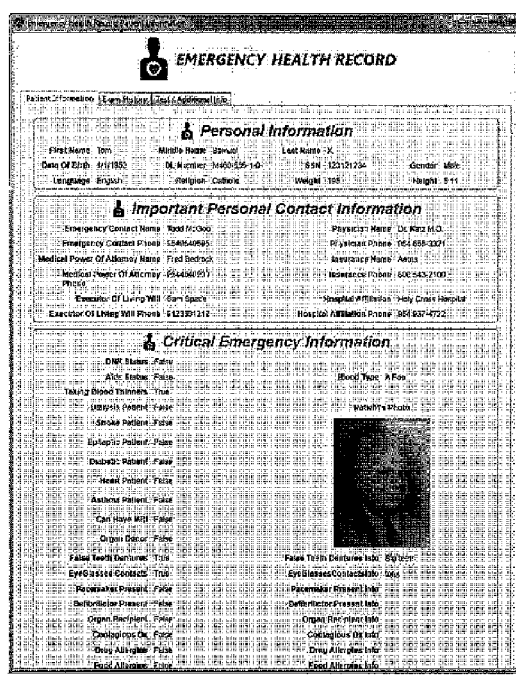
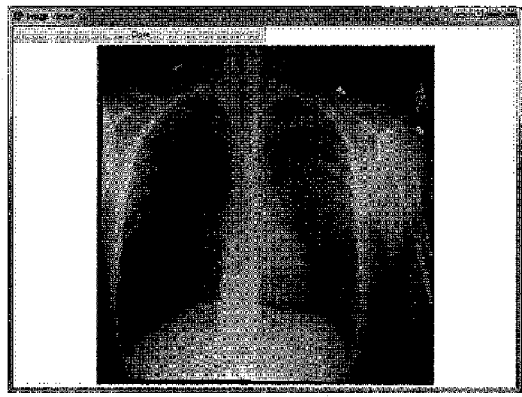

ENCRYPTED PORTABLE ELECTRONIC MEDICAL RECORD SYSTEM

CROSS REFERENCE TO RELATED APPLICATIONS

This application claims the benefit of provisional patent application Ser. No. 61/315,527 filed Mar. 19, 2010.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

This invention relates generally to an electronic record system, and more particularly, to an electronic medical record device and management system that is encrypted to authenticate, authorize and deny access to the system and patient information based on a user's encryption security level, facilitates electronic updating of patient information on the device and in the system by authorized users and manages the storage, flow and access to medical information stored in a database or data warehouse.

2. Description of the Background Art

Patient medical information, dental information, personal information, insurance information, charts and diagnostic test results have been traditionally maintained in paper medical files or in some respects on a computer system, and managed by the doctors' offices. The problem with traditional systems and methods is that only the patient's doctor has access to personal information and other doctors and medical personnel do not have immediate access when they may need it to treat a patient, especially in emergencies. Right now, hospitals and doctor offices do not share medical information electronically and do not have the ability to access a patient's medical and related information outside of their own internal system. To obtain needed patient medical information, a doctor or medical personnel must try to locate a patient's doctor and wait for the information or spend time tracking down needed medical and related information. If unsuccessful, the medical personnel must run tests, which may not be needed or may administer medical treatment or medicine that is detrimental to the patient. This is not only financially costly, but it cost a patient's life.

When a patient is treated by emergency medical personnel at a remote location or in a hospital emergency room, doctors want and need to know important medical information of the patient to properly treat them without risking harm or even death to the patient. Attending physicians and nurses need to know what medications the patient takes, whether the patient is allergic to any medicine or has any diseases, heart disease or any other relevant health condition. If a patient is in a comatose state, unconscious or unable to recall their doctor's name or their actual medical history and information, it makes it much more difficult and dangerous for the attending physician to administer care. In these situations, prior to treating the patient, the attending physician has to spend time, energy and resources to determine a patient's medical status. This increases the costs of treating a patient and greatly increases the risk of additional suffering by the patient, permanent health consequences or even potential death.

Attempts have been made to create medical cards and systems with electronically stored medical information of a person that can be accessed electronically and a universal medical information system. These devices and systems, however, have not been adopted by the medical community for several reasons. For instance, current medical information cards known are easily manipulated as they are not encrypted to control access. Conventional medical cards also fail to satisfy HIPAA requirements because they are not secure, are unreliable and easily manipulated by the owner or caring medical personnel. Accordingly, medical doctors and nurses do not and cannot rely on the health information contained on a patient's medical card.

There are many patents and published patent applications that disclose a variety of medical health cards and record systems, but they fail to adequately and effectively address these reliability and accessibility issues as contemplated by the instant invention disclosed herein. Accordingly, they have not been adopted for mainstream use or for use to make the medical record industry electronic. For instance, U.S. Pat. No. 7,395,215, issued to Grushka, discloses a portable personal health information package comprising a database management software program and portable computer readable storage device wherein the owner has absolute control on the availability, completeness, accuracy, integrity, confidentiality, security, backups and access to his health data. U.S. Pat. No. 6,662,999, issued to Vancour et al., discloses a system and method for generating an identification card with information regarding providers, eligibility, the client, benefits and business rules to reduce errors in exchanging data, U.S. Pat. No. 6,488,205, issued to Jacobson, discloses a system and method for extracting and processing data on an information card, particularly a healthcare plan identification card, wherein the system associates the data with a healthcare plan sponsor, analyzes the data to determine a healthcare plan product identifier and provides information about the healthcare plan so that decisions can be made about an individual associated with the healthcare plan. U.S. Pat. No. 6,021,393, issued to Honda et al., discloses a medical information management system including a portable memory card carried by a patient to store personal medical information and a read/write drive for the card that includes an optical head, a carrier mechanism for loading the memory and a coupler section for coupling electronic information to be read and written from the integrated circuit memory so that reading and writing of optical information can be conducted simultaneously with reading and writing electronic information. U.S. Pat. No. 5,899,998, issued to McGauley et al., discloses a method and system for maintaining and self-updating computerized medical records that employs point-of-service stations disposed at convenient medical service locations, wherein each patient carries a portable data carrier such as a smart card that contains the patient's complete medical history and interacts with the point-of service stations that effects a virtual communication link to tie the distributed databases together without need for online or live data connections. U.S. Pat. No. 5,822,544, issued to Chaco et al., discloses a patient care and communication system that utilizes a central processing system and a plurality of remote stations electrically connected to the central processing system to facilitate audio, visual and data communications. U.S. Pat. No. 5,724,379 issued to Perkins et al., discloses a method of modifying comparable health care services by comparing health care services from different providers independently of the clinical complexity of treating the diseases of the patients involved. Lastly, U.S. Pat. No. 3,970,996, issued to Yasaka et al., discloses an apparatus for collecting and recovering medical data which allows a number of different patients to be identified by an ID card or label and has a plurality of keyboard printing units and memory for receiving medical data as well as a control unit for controlling the input and output units. While the foregoing patents disclose a variety of medical cards and medical data systems, they all fail to provide a reliable and effective medical data record system that is reliable, encrypted and secure in HIPPA compliance so as to provide an accepted electronic medical record system for widespread use by the medical profession and insurance companies, as contemplated by the instant invention.

As noted, there are also a many published patent applications that disclose a variety of medical health cards and record systems, but they too fail to adequately and effectively address the reliability and accessibility issues of devices and systems. For instance, U.S. Patent Pub. No. 2009/0164243, filed by Zubak et al., discloses a system and method for generating healthcare identification and reconciliation information, wherein the system receives input data representative of a participating user's benefit plan, patient data, network data, insurance/payor data and healthcare provider data. U.S. Patent Pub. No. 2009/0144200, filed by Yoshioka, discloses a medical care record management system, medical care record management program and medical care record management method that acquires medical care information from a medical institution that conducts care for an insured patient and information that integrates medical and insured patient information with insured patients' signatures and medical institutions' signatures. U.S. Patent Pub. No. 2009/0019552, filed by McLaughlin et al., discloses a healthcare medical information management system for providing access to healthcare records that includes a database system comprising patient healthcare records, a healthcare workstation coupled to the database system and an authentication system that generates a fingerprint image of the patient at the point of treatment and a corresponding identification number and compares the number to a corresponding patient. U.S. Patent Pub. No. 2008/0319798, filed by Kelley, discloses a personalized medical information cared and method for managing same that includes creating an online medical information record that contains an individual's stored personal medical information, providing a credit card sized card which includes the individual's key medical information and enabling the individual to update their own medical information online. U.S. Patent Pub. No. 2008/0306774, filed by George et al., discloses a credit card sized digital storage device and data system for health care information including memory and a processor for processing digital data, an output on the card for converting and transmitting digital data for video output, a plurality of touch sensitive controls on the planar surface of the card and a wireless transmitter or a USB connector for physical connection to a computing device. U.S. Patent Pub. 2008/0183504, filed by Highley, discloses a point-of-care touch/click information entry system used for replacing or augmenting standard dictation transcription models in medical record systems and that uses key word entry to standardize medical record display. U.S. Patent Pub. 2008/0109261, filed by Kobayashi et al., discloses a method and apparatus for providing information that includes an updating unit that updates an electronic medical chart of a patient, an acquiring unit for acquiring information on recorded diagnosis and treatment from an updated medical chart, and an authenticating unit that authenticates the patient based on the acquired information. U.S. Patent Pub. No. 2007/0158411, filed by Krieg, Jr., discloses a method and system for storing, retrieving and updating information from an information card, wherein information on the card may be read from a magnetic reader and may comprise emergency tags, residential information tags, vehicle tags and retail tags. U.S. Patent Pub. No. 2007/0129969, filed by Burdick et al., discloses a system for entry of patient information for use by a medical office wherein the system comprises a patient data entry system that accepts direct electronic data input from patients through an in-office data entry system or through a web-based data entry system. U.S. Patent Pub. No. 2007/0088564, filed by March, Jr. et al., discloses a healthcare insurance claim processing system and method that generates a first set of data fields for display in a healthcare form. U.S. Patent Pub. No. 2007/0100664, filed by Seib et al., discloses an integrated healthcare and financial card comprising a magnetic swipe card having a magnetic stripe having at least two tracks for holding encoding data. U.S. Patent Pub. No. 2006/0111940, filed by Johnson et al., discloses a method and apparatus for assessing credit for healthcare patients prior to rendering treatment. U.S. Patent Pub. No. 2006/0074713, filed by Conry et al., discloses a patient identification card system and method for efficient medical care including a patient card, patient card access device and a medical report and a method for obtaining patient information using a patient card including inputting a request to a data processor, processing the request with the data processor and outputting the processed information to a medical report. U.S. Patent Pub. No. 2005/0197859, filed by Wilson et al., discloses a portable electronic data storage and retrieval system for health care data for a group, such as a household, that allows for the storage and retrieval of household level information in addition to individual household member data/information. U.S. Patent Pub. No. 2004/0199408, filed by Johnson, discloses a medical information card containing patient medical history information and medications in a form that is readable without a machine and includes a computerized system and method for producing the cards and updating information at a pharmacy where a new card is printed and presented. U.S. Patent Pub. No. 2003/0204417, filed by Mize, discloses an apparatus, method and system for the recordation, retrieval and management of pet information and use of same which provides membership-based selective access and retrieval of pet medical conditions, allergies and vaccinations and also includes pet owner spending habits. Lastly, U.S. Patent Pub. No. 2003/0220822, filed by Fiala et al., discloses a medical information registration and retrieval apparatus and method wherein a subscriber purchases database storage and enters medical information. While the foregoing published patent applications disclose a variety of medical cards and medical data systems, they also fail to provide a reliable and effective medical data record system that is reliable, encrypted and secure in HIPPA compliance so as to provide an accepted electronic medical record system for widespread use by the medical profession and insurance companies, as contemplated by the instant invention.

If there was a medical information system in existence that stored vital medical data and made portions of it available to medical personnel according to security clearance guidelines, it would be well received. However, there are no known medical information systems known that satisfy these requirements. Therefore, there exists a need for a medical information device and system that stores, controls and makes certain medical information available for access and updating according to predetermined security requirements. It is, therefore, to the effective resolution of the aforementioned problems and shortcomings of the prior art that the present invention is directed. The instant invention addresses this unfulfilled need in the prior art by providing an encrypted portable medical information device and system as contemplated by the instant invention disclosed herein.

BRIEF SUMMARY OF THE INVENTION

In light of the foregoing, it is an object of the present invention to provide an electronic medical record device and management system that is encrypted to authenticate and control access to a patient's medical history information.

It is also an object of the instant invention to provide an electronic and encrypted medical record device and management system that encryptically stores a patient's medical history information on a computer accessible medical record device.

It is another object of the instant invention to provide an electronic and encrypted medical record device and management system having a security system that identifies and controls the information available to requesting parties based on a predetermined level of security.

It is an additional object of the instant invention to provide an electronic and encrypted medical record device and management system that identifies and authorizes predetermined parties that can change a patient's information.

It is a further object of the instant invention to provide an electronic and encrypted medical record device and management system for storing and providing vital medical information for emergency medical treatment that is in HIPPA compliance.

It is yet another object of the instant invention to provide an electronic and encrypted medical record device and management system that provides immediate access to vital patient medical information.

It is yet a further object of the instant invention to provide an electronic and encrypted medical record device and management system that controls the data available to authorized requestors.

It is yet an additional object of the instant invention to provide an electronic and encrypted medical record device and management system having several layers of security.

In light of these and other objects, the instant invention comprises a portable, electronic and encrypted medical record device and management system that receives and stores a registrant's or patient's medical history in a secured database, records the medical history on a portable computer readable medical storage device, includes a multi-level encrypted security system to control access to the medical information on the storage device or in the system for authorizing modification or access to the medical information, allows authorized medical personnel to update recently acquired medical data, dictates the data that authorized medical entities or personnel have access to and includes a recognizable logo to alert medical personnel of the medical storage device. The instant invention is designed to accommodate current USB, magnetic and other data storage devices that may include necessary software for allowing or preventing access to its information or for updating information. The instant invention also contemplates various levels of encryption to control the information stored and available on the portable electronic and encrypted medical record devise.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 1 is a block diagram of the medical information device and system in accordance with the preferred embodiment of the instant invention.

FIG. 2 is a block diagram of the medical information device viewer and system in accordance with the preferred embodiment of the instant invention.

FIG. 3 is a block diagram of the medical information website and system in accordance with the preferred embodiment of the instant invention.

FIG. 4 is a block diagram of the medical information database/data warehouse and system in accordance with the preferred embodiment of the instant invention.

FIG. 5 is a block diagram of the medical information authentication and authorization provider in accordance with the preferred embodiment of the instant invention.

FIG. 6 is a block diagram of the web client interaction with the medical information device and system in accordance with the preferred embodiment of the instant invention.

FIG. 7 is a block diagram of the logging provider in accordance with the preferred embodiment of the instant invention.

FIG. 8 is a block diagram of the reporting engine in accordance with the preferred embodiment of the instant invention.

FIG. 9 is a block diagram of the third party extraction transformation and loading (ETL) in accordance with the preferred embodiment of the instant invention.

FIG. 10 is a block diagram of the web services application programming interface (API) in accordance with the preferred embodiment of the instant invention.

FIG. 11 is a block diagram of the scheduled services provider in accordance with the preferred embodiment of the instant invention.

FIG. 12 is a detailed block diagram of the open and viewing of the encrypted test file from the medical information device in accordance with the preferred embodiment of the instant invention.

FIG. 13 is a detailed block diagram of downloading and saving encrypted patient information from the web service to the medical information device in accordance with the preferred embodiment of the instant invention.

FIGS. 14a-14c depicts the type of form and information stored on the medical information device and in the system in accordance with the preferred embodiment of the instant invention.

FIGS. 15a and 15b depict all the different medical information device application screen shots of the system in accordance with the preferred embodiment of the instant invention.

FIG. 1 is a block diagram of the medical information device and system in accordance with the preferred embodiment of the instant invention.

DETAILED DESCRIPTION OF THE INVENTION

With reference to the drawings, FIGS. 1 to 15b depict the preferred embodiment of the instant invention which is generally referenced as a medical information device and management system and, or by numeric character 1. With reference to FIGS. 1-13, the instant invention is an encrypted portable electronic medical device and system 1 generally comprising a patient medical record stored on a USB card 16, an authorization server 5, web services 10, at least one secured database 414 and a storage array network server 415. With reference to FIGS. 14A-14C, the medical information device 16 comprises vital medical health information as shown on the Emergency Health Record (a trademark of the applicant) form 14A. This information may vary and include other information, such as dental and personal information, without departing from the scope and spirit of the instant invention 1. The information stored on the device 16 is encrypted on the device 16 and in the system 1 so that only authorized medical personnel may access or change the information on the card 16. While a patient/client may access the information on their device 16, only their doctor or other authorized medical attendant may change the information on the card 16. This insures that a client cannot inadvertently enter incorrect information and prevents others from changing that information. The medical information on the device 16 and in the system 1 is secured and confidential in compliance with HIPAA. The instant invention 1 comprises various levels of authorization. For instance, all the data available to a client's doctor may not be available to an insurance agent, pharmacy or lab. The instant invention 1 is designed to offer multiple authorization levels. The purpose of the instant invention 1 is to provide vital medical health information of a patient to an attending physician or other medical personnel, such as EMS or hospital emergency room physician, that is normally only known or available to a patient's primary doctor. In the event of a medical emergency, the device 16 will be instantly recognized as a standard medical information card in the medical community. The instant invention 1 may also include a sticker on a client's motor vehicle or other indicia that indicates to an attending medical person that the patient has a medical information device 16, in the event the patient is unconscious. The medical information device 16 and system 1 also provides a central secured database 414 and software that allows doctors, hospitals, insurance companies, pharmacies, labs and other medical related companies to access and share medical information on patients or clients. With reference to FIGS. 1-13, the medical information system 1 comprises a patient medical record encrypted and stored on a USB device 16. The USB device 16 may be secured on a card, wrist band or any other practical device that allows an attending physician to plug it into a USB drive on a computer to access the information on the device. The USB device 16 is plugged into a computer so as to electronically communicate with an authentication and authorization provider 5. Referring to FIG. 1, the authentication and authorization provider 5 comprises a web site 3, logging provider 7 and database 4. The authentication and authorization provider 5 validates a person attempting to log into the system 1, the authentication and authorization provider 5 determines whether a patient is current and registered, the logging provider 7 tracks the activity on a client's account and the database 4 stores the requisite medical data. A user opens a web client 6 accessing the system 1 does so through the Internet, which connects one to the website 3.

With reference to FIG. 2 when the PMD application 201 is started there is a check for web service connectivity 202. If there is no connectivity the PMD application will update the status bar to red light and show the user a notification dialog stating no connectivity is available 203. The PMD application will notify user of the manual login procedure clicking next opens manual login procedure process 204. The manual login process begins by displaying a phone number and a generated pass code 205. Instruct the user to call the phone number to get the unlock code either by operator assisted or automatic system 206. When unlock code is entered and click open patient info the limited view of patient data is viewable 207. If there is web service connectivity download encrypted files to PMD local storage 210. All patient data and test files have been updated on the PMDs local storage 212. The user has been authenticated and the PMD has been notified of this user's authorization level 213. If the user does not have full authorization 214 the user can only view the critical emergency information available under the first section 215 and 1502. The patient data file is decrypted but due to this authorization level sensitive fields and tabs are disabled 216 and 1502. If the user has full authorization 214 then the user has access to view the other 2 sections latest exam history 1505 and all test results 218, 1506. The patient data file is decrypted and because of this authorization level sensitive fields and tabs can be viewed 219. In addition this authorization level can view all test metadata and the actual test results in the image viewer 220 and 1507.

With reference to FIG. 3, accessing the web site with a web client browser. EMS/Physician/ER personnel uses web browser client to access website 302. The secure login process is initiated by passing credentials to the web server 303. Credentials NOT valid, Reject Login 305. Credentials are Valid; the user is then authenticated and authorized allowing a specific level of information 306. EMS can only see information from page 1 limited view 316. Once logged in user can search for a patient 307. On the patient Admin screen the physician can maintain the following information 308. View/Add/update/Delete critical & other info 309. Page 1 Section 1, 2 and 3 310. View/Add/update/Delete Exam info 311. Page 2 312. View/Add/update/ Delete Test info 313. Page 3 With file upload From Hosp. Labs Pharmacy etc. 314.

With reference to FIG. 4, the database/data warehouse consists of replicated relational database management server 414 residing on a replicated Storage Area Network 415. Access is obtained via Website Data Objects and Web services 401. The Data Access Layer 402 consists of: C# Structures, CRUD methods for all tables 403, Stored procedures to prevent SQL injection 404 and web service provider to integrate with 3rd party data objects 405. The Patient information stored consists of: Critical emergency information 407, Exam history 408 and Test information 409. Authentication information 410: Full user identity information, password and access level 411. Logging information 412, DT stamp, IP Computer name Browser Current login user. Mirror tables for all critical operations 413.

With reference to FIG. 5, Authentication and Authorization Provider starts with: Authentication Method called with credential username and password 502. Authentication method calls database to verify credentials 503. Credentials NOT valid 504 Return login false and access level 0 508. Credentials are valid 504 Query user id for access level 505, Return login true and user access level 508.

With reference to FIG. 6, web client; User opens browser of choice 602. Internet Explorer, FireFox, Chrome, Safari, Opera etc. 603. Enter URL in address field 604. Login with user credentials 605. Perform website functions 607. Log out of web site, Close browser 609.

With reference to FIG. 7, logging provider; if this is web site logging then log activities and transactions from the E.H.R. Web Site 703. Log activities and transactions from the E.H.R. WEB Service 704. Logging provider adds new record to logging tables for required transactions 705. Updates E.H.R Database/Data Warehouse 706.

With reference to FIG. 8, reporting engine purpose is: Reporting Engine runs standard reports or reports generated by users 802. Scheduled Services Engine to run future or recurring reports 803. Scheduled report queue, Run report 804. Data Access Layer to return report data to Report Engine 805. E.H.R Database/Data Warehouse 806. Reports run are delivered via file system, email, FTP etc. 807.

With reference to FIG. 9, the information can be imported into the database/data warehouse 4 via the third party extraction transformation and loading (ETL) services 9. The data fields are mapped 904 and 908 between multiple sources such as doctor's office database, patient medical information database, hospital database, EMS database, insurance database, pharmacy database, laboratory databases and others. Depending on the agreement with the external data provider 910 the data can be pushed 905 from the third party data source 910 to database 414 via web services 906 or pulled 907 from the third party data source 910 via web services 906 and added to the database 414.

With reference to FIG. 10, web services 10 purpose is to provide an external interface to Portable Medical Device (PMD) 2. E.H.R Web Site 3. E.H.R Database and Data Warehouse 4. 3rd Party Extraction Transformation Loading Web Service interface 9.

With reference to FIG. 11, scheduled services, monitor for Reporting Engine job scheduling 1103. User appointment notification job scheduling 1104. 3rd Party Extraction Transformation Loading (ETL) job scheduling 1105.

With reference to FIG. 12, PMD test file read, decrypt and view: PMD application executing with authenticated user with full authorization 1202. User clicks on the Test/Miscellaneous tab to access previous tests 1203. User clicks on one of the latest images or a link from a previous test from the lists below 1204. The view file window is opened with a link to a reference encrypted file 1205. Because the files stored on the PMD are binary encrypted representations of an image 1206. The PMD application file method calls the web service for the decryption key 1207. The secure web service returns the decryption key 1208. PMD reads the binary file from local storage into a memory stream 1209. PMD decrypts the memory stream with returned decryption key 1210. The PMD then converts the byte array into a bitmap mage 1211. Populates the image control on the view file window 1212. The decrypted file is never written to isolated storage or the local file system 1213.

With reference to FIG. 13, encrypted patient data download: PMD is executing its internal application with web services connectivity 1302. PMD application reads patient owner ID from local configuration file for WEB service lookup 1303. User enters credentials to initiate the login process 1304. PMD calls authentication web service with the credentials supplied 1305. If credentials are not valid 1306 then reject login 1307. If credentials are valid then PMD calls Web service for patients pages 1, 2 and 3 with PMD owner ID 1308. Web service returns patients pages 1, 2 and 3 encrypted 1309. PDM application writes encrypted patient data to local storage 1310. PMD calls WEB Service file name list method with PMD owner ID 1311. WEB Service returns list of test files related to the PMD owner 1312. PMD loops thru list of files. Calls WEB Service with ID for each filename 1313. WEB Service return the file in an encrypted binary stream 1314. PMD writes encrypted binary stream to a file on local storage 1315. Are there more files to process 1316? If yes 1313 if not Files Done 1317.

With reference to the drawings, the instant invention is an encrypted portable electronic medical device and system 10 generally comprising a patient medical record stored on a USB card 11, an authorization server 20-28, document management handler 30, at least one secured database 50 and a storage array network server 51. With reference to FIGS. 14a-15b, the medical information device 11 comprises vital medical health information as shown on the Emergency Health Record (a trademark of the applicant) form 11A. This information may vary and include other information, such as dental and personal information, without departing from the scope and spirit of the instant invention 10. The information stored on the device 11 is encrypted on the device 11 and in the system 10 so that only authorized medical personnel may access or change the information on the card 11. While a patient/client may access the information on their device 11, only their doctor or other authorized medical attendant may change the information on the card 11. This insures that a client does not inadvertently enter incorrect information and prevents others from changing that information. The medical information on the device 11 and in the system 10 is secured and confidential in compliance with HIPAA. The instant invention 10 comprises various levels of authorization. For instance, all the data available to a client's doctor may not be available to an insurance agent, pharmacy or lab. The instant invention 10 is designed to offer multiple authorization levels. The purpose of the instant invention 10 is to provide vital medical health information of a patient to an attending physician or other medical personnel, such as EMS or hospital emergency room physician, that is normally only known or available to a patient's primary doctor. In the event of a medical emergency, the device 11 will be instantly recognized as a standard medical information card in the medical community. The instant invention 10 may also include a sticker on a client's motor vehicle or other indicia that indicates to an attending medical person that the patient has a medical information device 11, in the event the patient is unconscious. The medical information device 11 and system 10 also provides a central secured database 50 and software that allows doctors, hospitals, insurance companies, pharmacies, labs and other medical related companies to access and share medical infatuation on patients or clients.

With reference to the drawings, the medical information system 10 comprises a patient medical record encrypted and stored on a USB device 11. The USB device 11 may be secured on a card, wrist band or any other practical device that allows an attending physician to plug it into a USB drive on a computer to access the information on the device. The USB device 11 is plugged into a computer so as to electronically communicate with an authorization server 20-28. Referring to FIG. 1, the authorization server comprises a web site 20, logon validation processing unit 22, patient validation server 24, tracking server 26 and database 28. The logon validation server 22 validates a person logging onto the system 10, the patient validation server 24 determines whether a patient is current and registered, the tracking server 26 tracks the activity on a client's account and the database 28 stores the requisite medical data. A user 12 or client 14 accessing the system 10 does so through the Internet, which connects one to the website 20. The medical information system 10 also comprises a document handler 30 that is accessed through the authorization server 20-28. The document handler 30 communicates with and provides controlled access to a plurality of databases, such as a doctor's office database 32, patient medical information database 34, hospital database 36, EMS database 38, insurance database 40, pharmacy database 42, laboratory databases 44 and others 46. Alternatively, all data may be stored on and accessed from one or main database. With reference to FIG. 4, patients, hospitals, pharmacies, police, fire rescue, diagnostic labs and, or doctors access the website 20 over the Internet 16 and through the authorization server 20-28. The authorization server 20-28 allows or denies access to the document management system 30.

With reference to the drawings, the system 10 comprises an authorization server 20-28 having a document policy manager system, document management system 30 and main database 50. The document policy manager is in two places simultaneously. Part A of the document policy manager resides on the document management side, working with the document handler. Part B of the document policy manager resides on the authorization side. When data records want to be accessed, Part B calls upon Part A for permission. If approved, Part A sends a key to Part B allowing access to and opening one or more parts within the data record. At the same time, Part A and B instructs the authorization server 20-28 to initiate its functions. Referring to FIG. 5, the document management system 30 comprises a document creator system 62, document storage system 64, document handler system 66, Part A of the document policy manager system 68 and a storage array network controlled server 51 (the "SAN system"). The document creator system 62 pulls information from data sources, then constructs a file based on the data received. Once the file is made, the document creator transmits the file to the document storage system 64. The document storage system 64 selects the record folder for placing the file received from the document creator 62. Once the files are placed in the record folder, the folder is passed to the document handler system 66. The document handler system 66, scans the record folder for any updates that may have been placed in the folder. The document handler system 66 waits for the document policy manager (Part A) 68 before sending the record folder to the SAN system 51. Once the document creator system 62 and document storage system 64 transmits the data, the document handler system 66 continues to hold the folder while it waits for the file-by-file access assignment as determined by the document policy manager system 68. When this done, the document policy manager 68 releases the record to the document handler system 66 for placement in the SAN server 51. The SAN system 51 stores the most updated record fold at all times.

With reference to the drawings, the document policy manager 68 simultaneously resides in two locations. Part A resides on the document management system 30 side to work with the document handler 66 and Part B resides on the authorization server 20-28, i.e. the authorization side. When a data record wants to be accessed, Part B calls upon Part A. For permission, Part A passes a key to Part B allowing designated parts of the dat record to be opened or accessed. At the same time, Part A and Part B instruct the authorization server 20-28 to start its functions. Part B of the document policy manager system 68, i.e. authorization server, comprises a server tracking system 70, server login password system 72, server update manager system 74 and management schema 76 in the server tracking system 70. The only way to access the web server 20-28 is through the data record schema 76 in the server tracking system 70. The server login password system 72 tracks local IP addresses and record header data, such as date and time, to determine who is accessing the system 10, what information is being sought, why the information is needed and when it is being requested. When data outside the system 10 is trying to be accessed, the server login password system 70 generates a "logon script" that places the user in one of three positions, i.e. patient mode, practitioner mode and, or emergency mode. Once one of the three modes is established, the login password system 72 contacts the document policy manager system 68 for keys to pass along to the logon scrip found in the data record. This allows access to the files needed within the data record. It is important to note, that the tracker server monitors everything going on during a session. The login password system 72 works with the document policy manager system 68 to determine which files within the record may be accessed. The server update manager system 74, scans the data record for file updates that need to be placed in the data record. The update manager 74 also checks file size and conductivity speed for download. The update manager system 74 makes a call to the login script to notify the user of updated data. The management schema 76 has full control over all operations of the document policy manager system 68 and collects data that tracks the progress of the system 10.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

What is claimed is:

1. An encrypted medical information system for storing and facilitating access to medical information of an individual, said system comprising:
a portable medical information storage device comprising a computer readable storage device having medical data for an individual;
a multilevel password system comprising a plurality of encryption codes for selectively controlling access to predetermined portions of said medical data, said encryption codes being stored on said portable medical device and comprising:
a personal patient password code that allows the personal patient to view its corresponding medical data without the ability to change said medical data anti to view and edit personal identification information;
a provider password code that allows a medical provider to modify and view predetermined portions of said patient medical data on said portable medical device; and
an emergency medical password code that limits access to predetermined medical data required to render life-saving or life-changing medical treatment;
an authentication means, on said portable medical information storage device, for authenticating said encryption codes wherein said portable medical information storage device does not require an external server for encrypting and decoding;
a set of computer processor readable code for communicating data to and from said storage device;
means, in communication with said set of computer processor readable code, for allowing and controlling access to said medical data based on said encryption codes; and
database for storing said medical data.

2. A system as recited in claim 1, wherein said portable computer readable storage device comprises:
a USB device.

3. A system as recited in claim 1, further comprising:
a form stored on said portable medical device comprising medical data on a patient electronically stored in said system;
said form comprising electronically identified fields for storing and accessing predetermined data.

4. A system as recited in claim 1, further comprising:
an authorization server comprising an authentication list having said encryption codes and only being accessible to create or modify said authentication list.

5. A system as recited in claim 1, further comprising:
a document handler.

6. A system as recited in claim 1, further comprising:
a document management system.

7. A system as recited in claim 1, further comprising a database.

8. A system as recited in claim 1, further comprising a portable medical device information viewer.

9. A system as recited in claim 1, further comprising a portable medical device test file reader and viewer.

10. A system as recited in claim 1, further comprising a portable medical device encrypted data update process.

11. A system as recited in claim 1, further comprising an authentication and authorizer provider.

12. A system as recited in claim 1, further comprising an emergency record reporting engine.

13. A system as recited in claim 1, further comprising, a third party extract transformation and loading program.

14. A system as recited in claim 1, further comprising an emergency logging provider.

15. A system as recited in claim 1, further comprising a data warehouse.

* * * * *